(12) United States Patent
Komoda

(10) Patent No.: US 11,006,873 B2
(45) Date of Patent: May 18, 2021

(54) CALCULATING A SCORE OF A DEGREE OF AROUSAL OF A USER

(71) Applicant: JINS HOLDINGS Inc., Maebashi (JP)

(72) Inventor: Taiki Komoda, Gunma (JP)

(73) Assignee: JINS HOLDINGS Inc., Maebashi (JP)

( * ) Notice: Subject to any disclaimer, the term of this patent is extended or adjusted under 35 U.S.C. 154(b) by 0 days.

(21) Appl. No.: 16/487,575

(22) PCT Filed: Jan. 30, 2018

(86) PCT No.: PCT/JP2018/002929
§ 371 (c)(1),
(2) Date: Aug. 21, 2019

(87) PCT Pub. No.: WO2018/155098
PCT Pub. Date: Aug. 30, 2018

(65) Prior Publication Data
US 2019/0380637 A1 Dec. 19, 2019

(30) Foreign Application Priority Data
Feb. 22, 2017 (JP) ............... JP2017-031288

(51) Int. Cl.
*A61B 5/16* (2006.01)
*A61B 5/00* (2006.01)
*G06T 7/00* (2017.01)
*A61B 5/18* (2006.01)

(52) U.S. Cl.
CPC ............ *A61B 5/163* (2017.08); *A61B 5/0077* (2013.01); *G06T 7/0012* (2013.01); *A61B 5/18* (2013.01); *G06T 2207/30041* (2013.01)

(58) Field of Classification Search
None
See application file for complete search history.

(56) References Cited

U.S. PATENT DOCUMENTS 6,431,705 B1 * 8/2002 Linden .................. G02C 11/00
351/158
2010/0036290 A1 2/2010 Noguchi et al.

FOREIGN PATENT DOCUMENTS

| DE | 10 2008 007 152 A1 | 10/2008 |
| JP | H07-156682 A | 6/1995 |
| JP | 3127760 B | 11/2000 |
| JP | 2007-312824 | 12/2007 |

OTHER PUBLICATIONS

International Search Report and Written Opinion and English translation thereof dated Apr. 24, 2018 in connection with International Application No. PCT/JP2018/002929.
International Preliminary Report on Patentability and English translation thereof dated Sep. 6, 2019 in connection with International Application No. PCT/JP2018/002929.

* cited by examiner

*Primary Examiner* — G Steven Vanni
(74) *Attorney, Agent, or Firm* — Wolf, Greenfield & Sacks, P.C.

(57) ABSTRACT

To reduce errors in determining a degree of arousal due to variations in blinking among an individual or between individuals.
To execute the steps of: acquiring first biological information related to an ocular potential of a user from a processing device worn by the user; and calculating a degree of arousal of the user based on a distance between a projection axis parallel to an equal degree of arousal line and a point where the first biological information is plotted in a coordinate space where a height and width are the axes for an ocular potential peak.

9 Claims, 7 Drawing Sheets

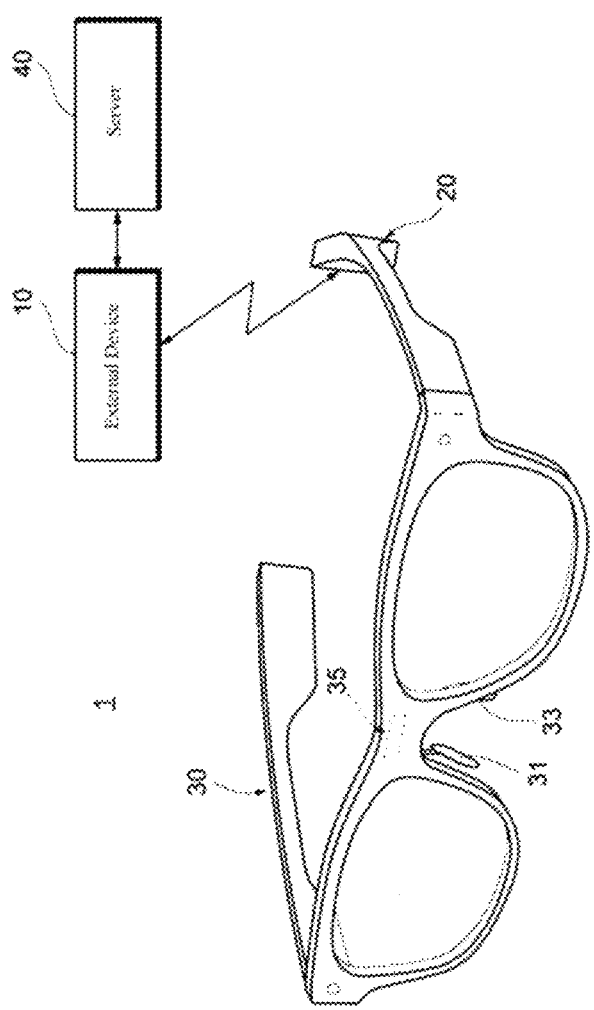
[FIG. 1]

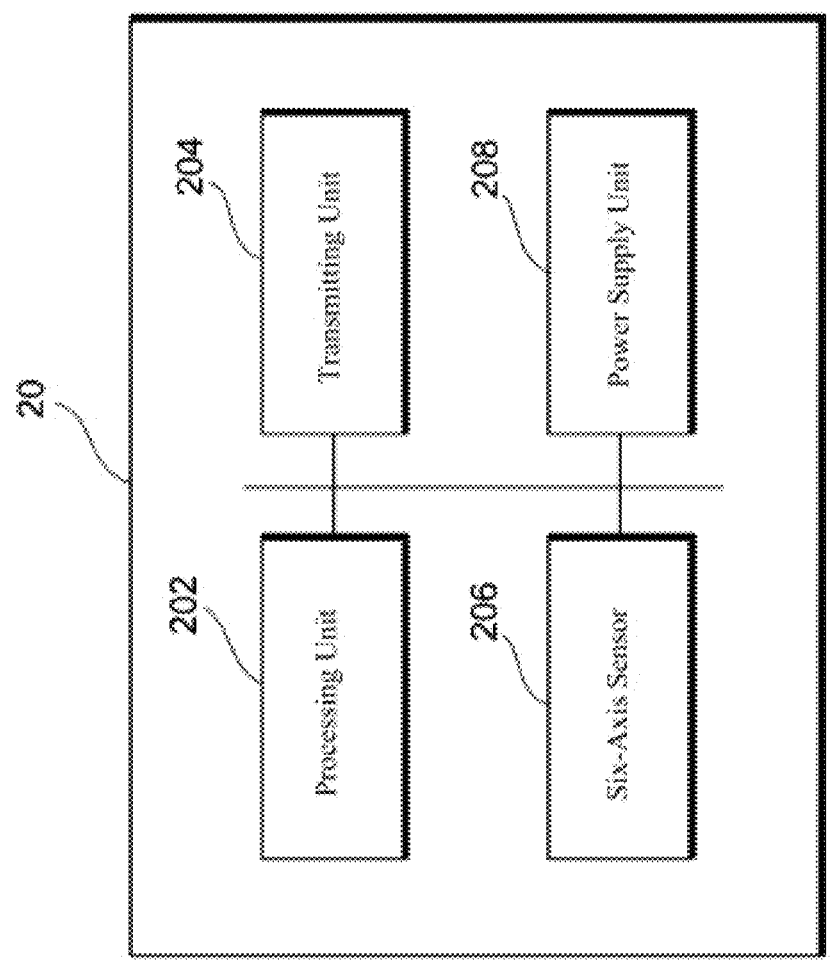

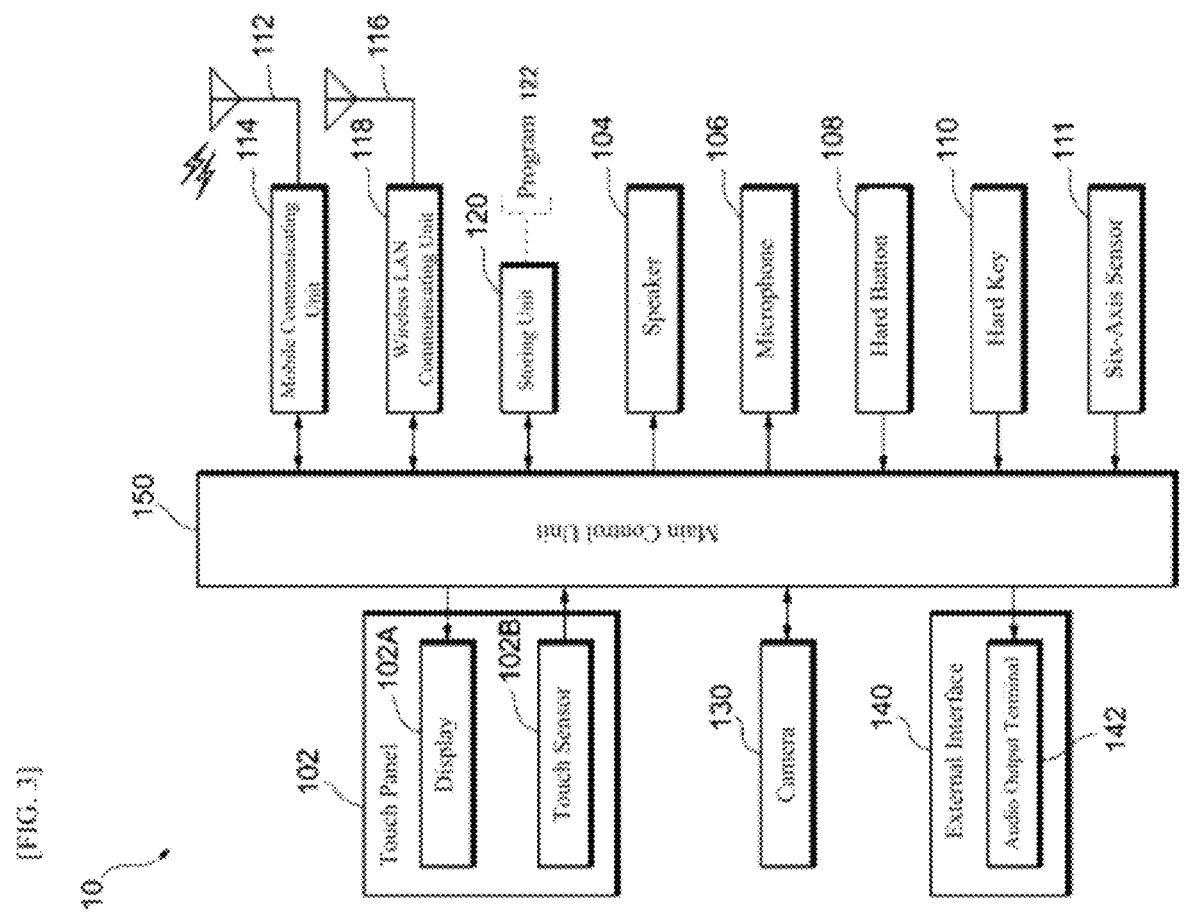
[FIG. 3]

[FIG. 4]
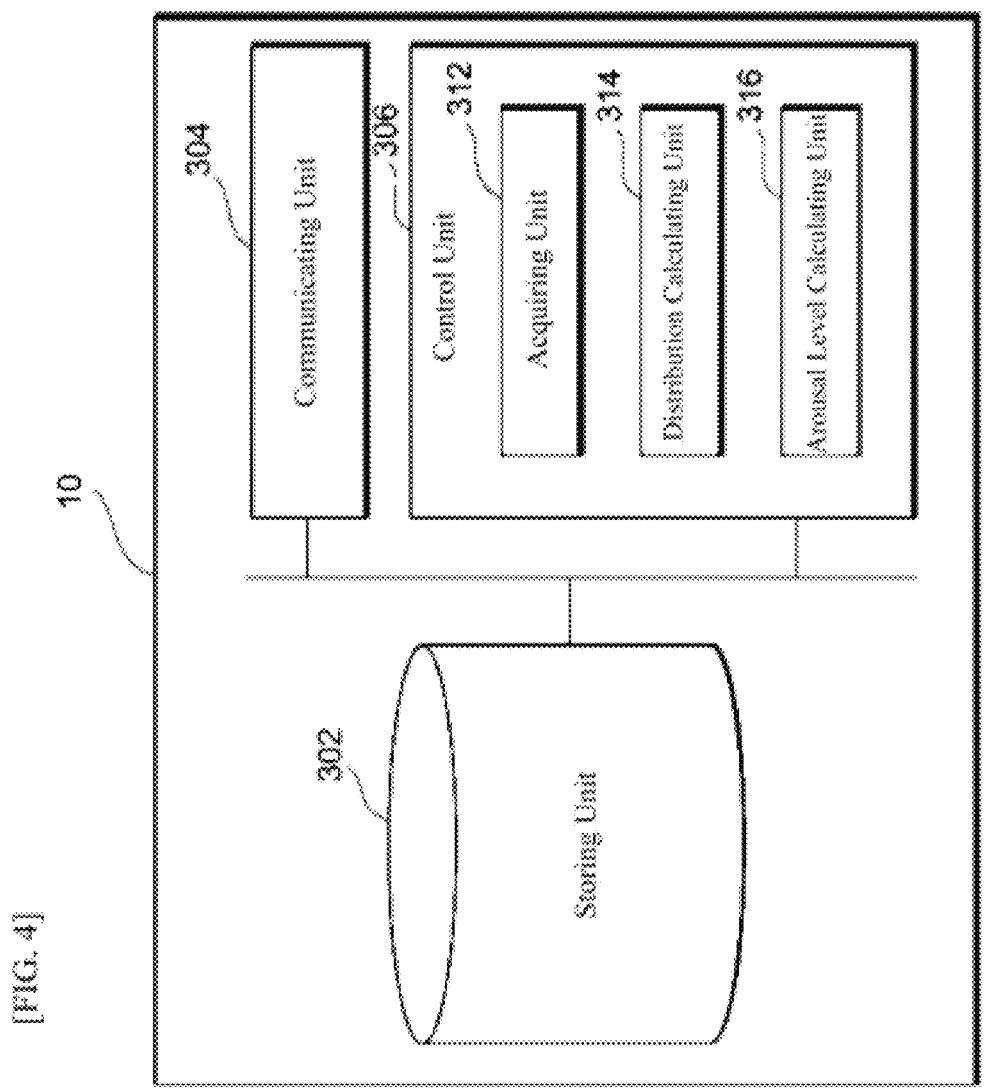

[FIG. 5]
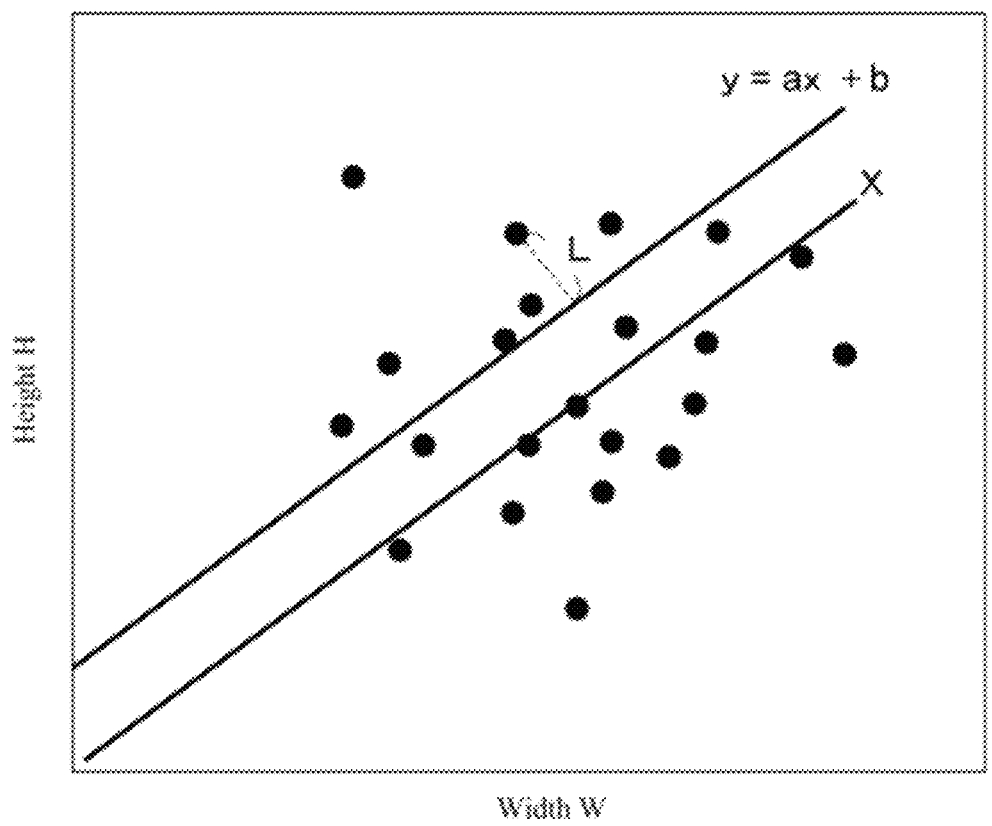
[FIG. 6]
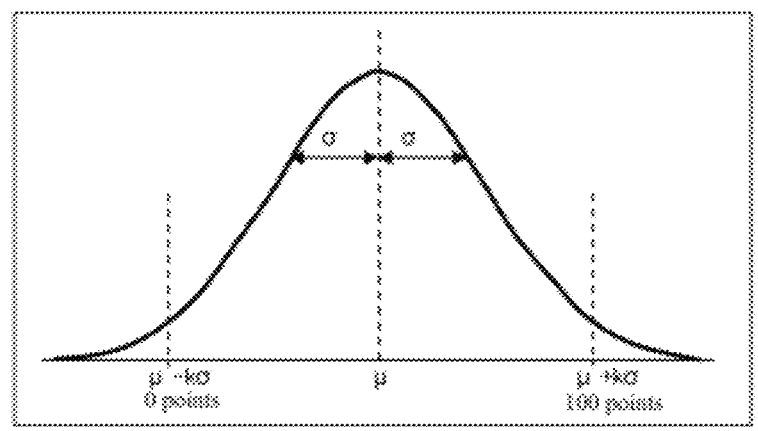

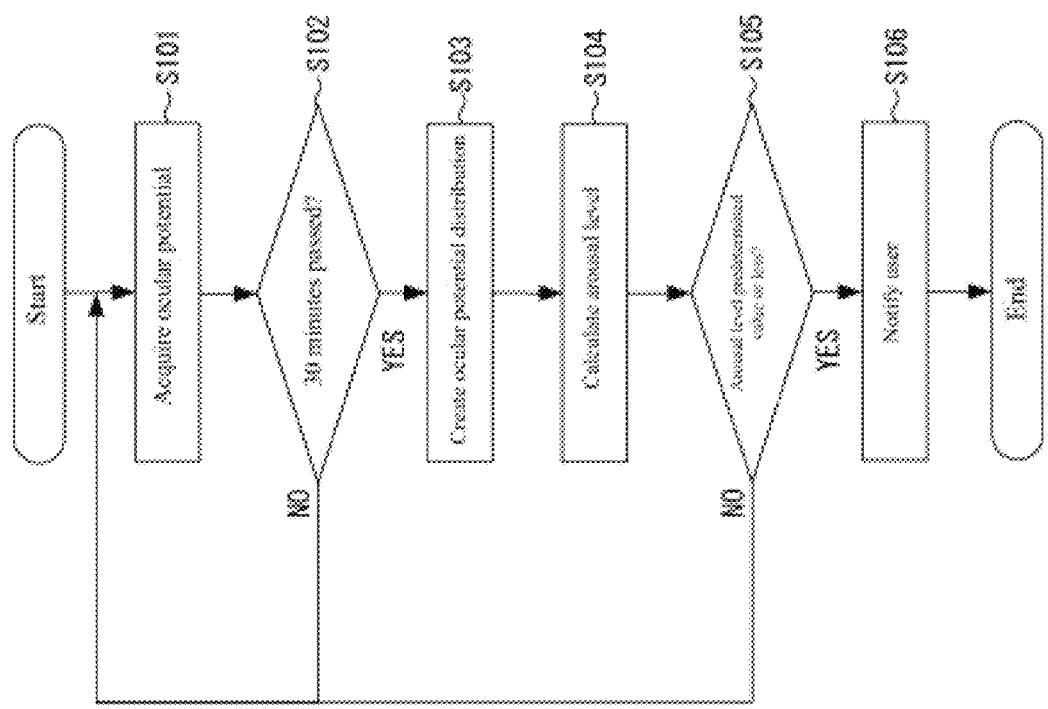
[FIG. 7]

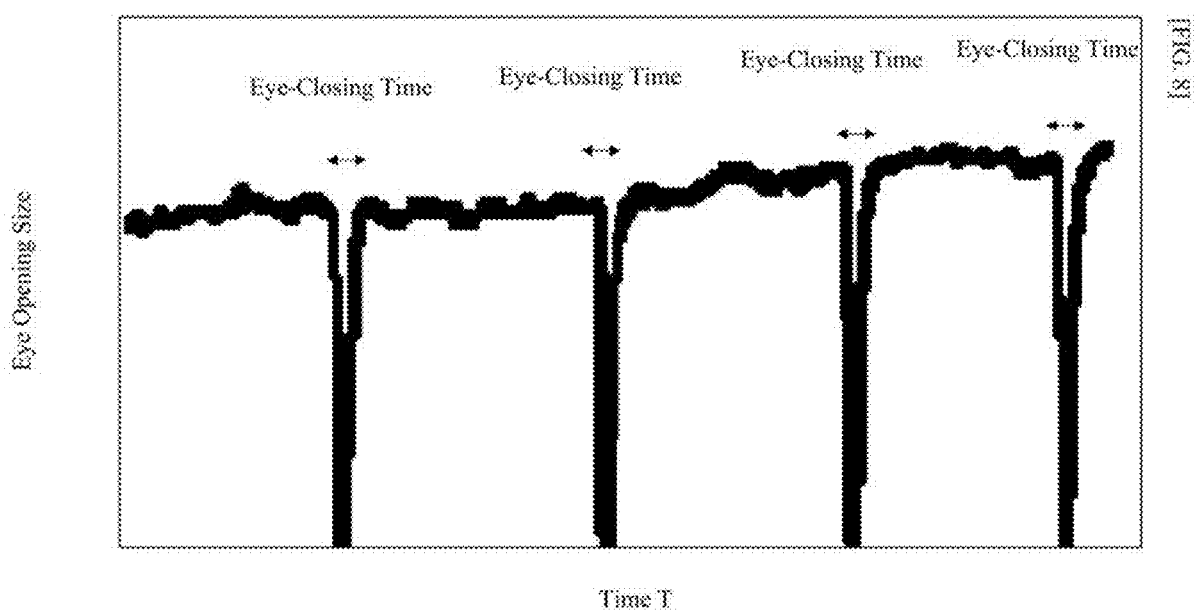

CALCULATING A SCORE OF A DEGREE OF AROUSAL OF A USER

CROSS-REFERENCE TO RELATED APPLICATIONS

This application is a national stage filing under 35 U.S.C. § 371 of International PCT Application No. PCT/JP2018/002929 filed Jan. 30, 2018, which claims priority to Japanese Application No. 2017-031288, filed Feb. 22, 2017. The entire contents of each of these applications are incorporated by reference herein in their entireties.

TECHNICAL FIELD

The present invention relates to an information processing method, information processing device, and program.

BACKGROUND ART

Conventionally, a device for improving a degree of arousal of an operator when a reduction in the degree of arousal from the operator is detected has been proposed. For example, with technology described in Patent Document 1, a degree of arousal of an operator is calculated based on a parameter extracted from a blink of the operator.

PRIOR TECHNOLOGY DOCUMENTS

Patent Documents

Patent Document 1: U.S. Pat. No. 3,127,760

SUMMARY OF THE INVENTION

Problem to be Solved by the Invention

Patent Document 1 discloses that an ocular potential may be used as a parameter. However, the width and height of an ocular potential peak fluctuates depending on the length and weakness of blinking, and therefore, variations among an individual and between individuals are large even if the degree of arousal is the same. Therefore, with conventional technology as in Patent Document 1, an error occurs in determining the level of arousal due to the variations among an individual and between individuals.

Therefore, an object of the disclosed technology is to reduce errors in determining a degree of arousal due to variations in blinking among an individual and between individuals.

Means For Resolving Problems

An information processing method of one aspect of the present disclosure is an information processing method executed by a computer, including the steps of: acquiring first biological information related to an ocular potential of a user from a processing device worn by the user; and calculating a degree of arousal of the user based on a distance between a projection axis parallel to an equal degree of arousal line and a point where the first biological information is plotted in a coordinate space where a height and width are the axes for an ocular potential peak.

Effect of the Invention

According to the disclosed technology, errors in determining a degree of arousal due to variations in blinking among an individual or between individuals can be reduced.

BRIEF DESCRIPTION OF THE DRAWINGS

FIG. 1 is a diagram illustrating an example of an information processing system in the examples.

FIG. 2 is a block diagram illustrating an example of a configuration of a processing device in the examples.

FIG. 3 is a schematic configuration diagram illustrating a hardware configuration of an information processing device in the examples.

FIG. 4 is a diagram illustrating an example of a configuration of an information processing device in the examples.

FIG. 5 is a graph used for degree of arousal calculation processing in the examples.

FIG. 6 is a graph used for degree of arousal calculation processing in the examples.

FIG. 7 is a flowchart showing an example of information processing in the examples.

FIG. 8 is a graph used for degree of arousal calculation processing in the examples.

DESCRIPTION OF THE PREFERRED EMBODIMENTS

An embodiment of the present invention will be described below while referring to the drawings. However, the embodiment described below is merely an example and is not intended to exclude the application of various modifications and techniques not explicitly described below. In other words, the present invention can be implemented with various modifications without departing from a gist thereof. Furthermore, in the following description of the drawings, the same or similar portions are denoted by the same or similar reference numerals. The drawings are schematic and do not necessarily correspond to actual dimensions, ratios, and the like. Portions with different dimensional relationships and ratios from each other may be included between drawings.

EXAMPLES

In the examples, eyewear is used as an example of a target for mounting an acceleration sensor, angular velocity sensor, and biological electrode. FIG. 1 is a diagram illustrating an example of an information processing system 1 in the examples. The information processing system 1 illustrated in FIG. 1 includes an external device 10, eyewear 30, and server 40. The external device 10, eyewear 30 and server 40 are connected through a network such that data communication is possible.

For the eyewear 30, a processing device 20 is mounted on a temple portion for example. The processing device 20 includes a three-axis acceleration sensor and three-axis angular velocity sensor (may be a six-axis sensor). Furthermore, the eyewear 30 respectively has a biological electrodes 31, 33, 35 on a pair of nose pads and a bridge portion. An ocular potential signal acquired from the biological electrodes provided on the eyewear 30 is transmitted to the processing device 20. The biological electrodes are provided for detecting blinking, visual line movement, and the like, but if blinking, visual line movement, or the like is detected by image processing, the biological electrodes may not be provided.

The processing device 20 transmits a sensor signal, ocular potential signal, and/or biological information calculated from these signals to the external device 10 and server 40. An installation position of the processing device 20 does not necessarily need to be a temple but is preferable considering balance when the eyewear 30 is mounted.

The external device 10 is an information processing device having a communication function. For example, the external device 10 is a mobile communication terminal such as a mobile phone, smartphone, or the like belonging to a user, a personal computer, table terminal, or the like. Based on the sensor signal, ocular potential signal, or the like received from the processing device 20, the external device 10 determines the degree of arousal of a user during operation and supports operation. The external device 10 will be described below as information processing device 10.

The server 40 acquires and stores information and the like related to the degree of arousal from the information processing device 10. The server 40 may be configured to directly acquire biological information, a sensor signal, an ocular potential signal, or the like from the processing device 20. In this case, the server 40 can transmit the sensor signal, ocular potential signal, or the like to the external device 10 based on a request from the information processing device 10 if necessary.

Configuration of Processing Device 20

FIG. 2 is a block diagram illustrating an example of a configuration of a processing device 20 in the examples. As illustrated in FIG. 2, the processing device 20 has a processing unit 202, transmitting unit 204, six-axis sensor 206, and power supply unit 208. Furthermore, the biological electrodes 31, 33, 35 are connected to the processing unit 202 using an electrical wire via an amplifying unit for example. Note that the parts of the processing device 20 may be provided not on one temple but distributed on a pair of temples.

The six-axis sensor 206 is a three-axis acceleration sensor and three-axis angular velocity sensor. Furthermore, these sensors may be separately provided. The six-axis sensor 206 outputs the detected sensor signal (also referred to as detected data) to the processing unit 202.

For example, the processing unit 202 is a processor that processes a sensor signal obtained from the six-axis sensor 206 or ocular potential signal obtained from a biological electrode as necessary and then outputs the signal to the transmitting unit 204. For example, the processing unit 202 can calculate biological information related to blinking or biological information related to visual line movement using the ocular potential signal. Note that the examples describe a case where the processing unit 202 outputs biological information related to an ocular potential signal to the transmitting unit 204.

Furthermore, the processing unit 202 calculates biological information related to body movement using a sensor signal from the 6-axis sensor 206. The biological information related to body movement, for example, is information indicating head movement within a predetermined time. For example, the processing unit 202 can generate data indicating a pitch angle, data indicating a roll angle, data indicating a yaw angle, and data indicating posture including the direction and magnitude of tilting of a body axis (hereinafter, collectively referred to as "head movement information") using the sensor signal from the six-axis sensor 206. Pitch angle indicates forward and backward deviation of the head for example. Roll angle indicates left and right deviation of the head for example. Yaw angle indicates left and right rotation of the neck for example. The direction and magnitude of tilting of a body axis indicates the direction and magnitude of tilting of the head for example. The pitch angle, roll angle, yaw angle, and posture may be calculated using a conventionally known technique. Furthermore, the processing unit 202 may simply amplify the sensor signal obtained from the six-sensor 206 or the like. Biological information related to blinking or visual line movement and head movement information will be described below using an example calculated by the processing unit 202. However, the information may be calculated by the information processing device 10 or server 40.

The transmitting unit 204 transmits information including biological information related to an ocular potential signal processed by the processing unit 202 and/or head movement information to the information processing device 10 or server 40. For example, the transmitting unit 204 transmits biological information related to blinking or visual line movement or head movement information to the information processing device 10 or server 40 by wired communication or wireless communication such as Bluetooth (registered trademark), LAN, or the like. The power supply unit 208 supplies power to the processing unit 202, transmitting unit 204, six-axis sensor 206, and the like.

Configuration of Information Processing Device 10
Hardware Configuration

FIG. 3 is a schematic configuration diagram illustrating a hardware configuration of an information processing device 10 in the examples. A typical example of the information processing device 10 is a mobile phone such as a smartphone or the like. However, electronic apparatuses having a touch panel such as a tablet terminal or mobile terminal capable of wireless or wired connected to a network and the like as well as general-purpose apparatuses capable of screen display while processing data while communicating using a network and the like can also correspond to the information processing device 10 according to the embodiment.

The information processing device 10 according to the embodiment, for example, is provided with a thin rectangular housing not illustrated in the drawings. A touch panel 102 is configured on one surface of the housing. Each component in the information processing device 10 is connected to a main control unit 150. The main control unit 150 is a processor for example.

A mobile communication antenna 112, mobile communicating unit 114, wireless LAN communication antenna 116, wireless LAN communicating unit 118, storing unit 120, speaker 104, microphone 106, hard button 108, hard key 110, and six-axis sensor 111 are connected to the main control unit 150. Furthermore, the touch panel 102, a camera 130, and external interface 140 are further connected to the main control unit 150. The external interface 140 includes an audio output terminal 142.

The touch panel 102 has both display device and input device functions, and is configured from a display (display screen) 102A responsible for the display function and touch sensor 102B responsible for the input function. For example, the display 102A is configured from a general displaying device such as a liquid crystal display, organic EL (Electro Luminescence) display, or the like. The touch sensor 102B is provided with an element for detecting a contact operation, which is disposed on an upper surface of the display 102A, and a transparent operating surface laminated thereon. An arbitrary system from already known systems such as capacitive type, resistive type (pressure sensitive type), electromagnetic guidance, and the like can be used as a contact detecting system of the touch sensor 102B.

The touch panel 102 serving as a displaying device displays an image of an application generated by executing a program 122 by the main control unit 150. The touch panel 102 serving as an input device detects an operation of a contact object (includes a player's finger, stylus, and the like. Hereinafter, a "finger" is described as a representative example) contacting the operating surface, and therefore, an operation input is received, and information of the contact position is provided to the main control unit 150. Movement of a finger is detected as coordinate information indicating a position or region of a contact point. The coordinate information is displayed as a coordinate value on two axes in a short side direction and long side direction of the touch panel 102 for example.

The information processing device 10 is connected to a network N via the mobile communication antenna 112 or wireless LAN communication antenna 116 such that data communication is possible with the processing device 20. Note that the storing unit 120 records the program 122. Furthermore, the storing unit 120 may be separate from the external device 10, and for example, may be a recording medium such as an SD card, CD-ROM, or the like.

Functional Configuration

Next the functional configuration of the information processing device 10 will be described. FIG. 4 is a diagram illustrating an example of a configuration of the information processing device 10. The information processing device 10 has a storing unit 302, communicating unit 304, and control unit 306.

The storing unit 302 can be implemented by the storing unit 120 or the like illustrated in FIG. 3 for example. The storing unit 302 stores data or the like related to an application (hereinafter, also referred to as "drive app") that manages the degree of arousal of the user in the examples. For example, the data related to the drive app is data received from the processing device 20 or server 40, data related to an equal degree of arousal straight line described later, data related to ocular potential distribution, or the like.

The communicating unit 304 can be implemented by the mobile communicating unit 114, wireless LAN communicating unit 118, or the like for example. The communicating unit 304 receives data from the processing device 20 or server 40 for example. Furthermore, the communicating unit 304 may transmit data processed in the information processing device 10 to the server 40. In other words, the communicating unit 304 has a function as a transmitting unit and receiving unit.

The control unit 306 is implemented by the main control unit 150 or the like for example, and executes the drive app. The drive app in the examples has a function of performing a notification if the degree of arousal of the user is reduced and determining whether or not the degree of arousal is improved due to the notification. In order to implement this function, the control unit 306 has an acquiring unit 312, distribution calculating unit 314, and degree of arousal calculating unit 316.

The acquiring unit 312 acquires biological information based on the ocular potential signal and head movement information based on the sensor signal from the six-axis sensor 206 worn on a human body. Note that "worn on a human body" not only includes directly wearing, but also includes indirectly wearing using a wearable device containing the eyewear 20 or the like.

The distribution calculating unit 314 calculates a histogram of the intensity (specifically, height and width during a peak) of an ocular potential of the user (hereinafter, also referred to as "ocular potential distribution") based on the acquired biological information. A method of calculating the ocular potential distribution will be described in detail while referring to FIG. 5. FIG. 5 is a graph showing a distribution of a measurement point of an ocular potential acquired from a target user. In FIG. 5, a vertical axis indicates the height of an ocular potential peak, and a horizontal axis indicates the width of the ocular potential peak. In the following description, the height of the ocular potential peak is also referred to as "height H", and the width of the ocular potential peak is also referred to as "width W". Note that for the ocular potential peak, the height H is reduced as blinking weakens, and the width W increases as blinking increases in length. In other words, an increase in the height H indicates that a user is not sleepy, and a reduction in the height H indicates that the user is sleepy. On the other hand, an increase in the width W indicates that the user is sleepy, and a reduction of the width W indicates that the user is not sleepy.

In FIG. 5, a straight line (hereinafter, also referred to as projection axis) as expressed by straight line y=ax+b is a straight line that is parallel to equal degree of arousal line X calculated in advance. The equal degree of arousal line X is determined by plotting measurement points of an ocular potential peak of a plurality of users who were determined to be the same degree of arousal in a space between the same height H and width W as those of FIG. 5. Specifically, the ocular potential of the measurement points is measured when the degree of arousals obtained by objective evaluation of an evaluator is determined to be in a condition where the same degree of arousal continues for a predetermined amount of time (for example, 10 minutes). Therefore, a region above the equal degree of arousal line X is plotted when a user is not sleepier than the equal degree of arousal line X. Conversely, a region below the equal degree of arousal line X is plotted when a user is sleepier than the equal degree of arousal line X. Note that the projection axis is only required to be parallel to the equal degree of arousal line X and, for example, may match the equal degree of arousal line X. Furthermore, in the example in FIG. 5, the equal degree of arousal line is a straight line. However, the line is not limited thereto and may be a curved line.

The distribution calculating unit 314 calculates a distance L to the projection axis in upper region of the projection axis and lower region of the projection axis for the measurement points of the ocular potential peak of the target user, acquired by the acquiring unit 312 during the determination reference period (for example, approximately 30 minutes) during user operation. The distribution calculating unit 314 calculates the ocular potential distribution, which is a histogram of the calculated distance L. Specifically, the distribution calculating unit 314 calculates the ocular potential distribution by determining an average ($\mu$) and standard deviation ($\sigma$) for the calculated distance. Note that in this case the distribution calculating unit 314 preferably excludes measurement points that are greatly separated from the projection axis as outliers.

FIG. 6 is a graph showing an example of ocular potent distribution calculated by the distribution calculating unit 314 by the above-said method. In FIG. 6, a horizontal axis indicates a distance calculated by the distribution calculating unit 314, and a vertical axis indicates a frequency that the distance is calculated. In the present example, it is assumed that the ocular potential distribution is a normal distribution as shown in FIG. 6. In this case, a vertex of the normal distribution indicates an ocular potential that is most likely to occur during operation of a target user, the distance in the upper region of the projection axis is distributed to a right side of the normal distribution and the distance in the lower region of the projection axis is distributed to a left side of the normal distribution. The distribution calculating unit 314 can convert and handle the ocular potential peak as one-dimensional data from second-dimensional data of the height H and width W by converting the ocular potential distribution.

The degree of arousal calculating unit 316 scores the degree of arousal of the user based on the ocular potential distribution calculated by the distribution calculating unit 314. Specifically, the degree of arousal calculating unit 316 calculates a distance between a measurement point and projection axis when the measurement point is plotted on the graph in FIG. 5, based on the height H and width W of the ocular potential of the user acquired by the acquiring unit 312 during an operation. Next, the degree of arousal calculating unit 316 scores the degree of arousal based on which position on the horizontal axis for the ocular potential distribution in FIG. 6 the calculated distance corresponds to. Specifically, the degree of arousal calculating unit 316 performs linear conversion such that the range of ±k (constant)×σ on the horizontal axis for the ocular potential distribution is within a range of 0 points to 100 points, and then scores the degree of arousal. In this case, 50 points corresponds to the most average degree of arousal during operation by the user. Furthermore, 100 points corresponds to the highest degree of arousal, and 0 points corresponds to the lowest degree of arousal. For example, when it is assumed that the user is sleeping when the degree of arousal is included in the lower 5% of the ocular potential distribution, it is determined that the user is very sleepy when the degree of arousal is a score of 5 points or less.

Note that the degree of arousal calculating unit 316 preferably calculates the moving average from the measurement point of the ocular potential during a predetermined period (for example, 2 minutes) for the distance between the measurement point and projection axis. Thereby, higher precision calculation of the degree of arousal can be performed.

The degree of arousal calculating unit 316 preferably determines whether or not the calculated degree of arousal is lower than a predetermined value, and then notifies the user when it is low. This notification can be performed by sound, vibration, or the like for example.

The height H or width W of the ocular potential peak changes based on the length or weakness of blinking, and therefore may change even if the degree of arousal is the same. On the other hand, a ratio between the height H and width W is constant if the degree of arousal is the same. Therefore, the distribution calculating unit 314 calculates the ocular potential distribution based on the projection axis parallel to the equal degree of arousal line X, and therefore, errors in determining the degree of arousal due to variations in blinking among an individual and between individuals can be reduced.

Operation

Next, an operation of the information processing device 10 in the examples will be described. FIG. 7 is a flowchart showing an example of an entire process of an application in the examples.

First, the acquiring unit 312 acquires an ocular potential for a predetermined time (30 minutes in this example) from the user during operation (S101). When the predetermined period has passed (S102: YES), the distribution calculating unit 314 creates an ocular potential distribution (see FIG. 5) from the ocular potential acquired during the period (S103).

When the ocular potential distribution is created, the degree of arousal calculating unit 316 calculates the degree of arousal of the user based on the ocular potential acquired by the acquiring unit 312 while referring to the ocular potential distribution (S104).

The degree of arousal calculating unit 316 determines whether or not the calculated degree of arousal of the user is a predetermined value or less (S105). When the degree of arousal of the user falls to a value equal to or below the predetermined value (S105: Yes), the degree of arousal calculating unit 316 notifies the user via sound and/or vibration (S106). On the other hand, when the degree of arousal of the user does not fall below the predetermined value (S105: Yes), the process returns to step S101.

The control unit 306 repeatedly executes the processes from S101 to S106 during activation of the application.

According to the examples as described above, errors in determining a degree of arousal due to variations in blinking among an individual or between individuals can be reduced.

Note that in the examples, a case where the eyewear 30 was glasses was described. However, the eyewear is not limited thereto. The eyewear may be an apparatus related to eyes or may be an apparatus attached to the face or apparatus attached to the head such as glasses, sunglasses, goggles, head-mounted displays, frames thereof, or the like.

Furthermore, in the examples, a case where the eyewear 30 was provided with a biological electrode and six-axis sensor was described. However, as described above, for example, an image (static image or moving image) of the user during operation is acquired from a high-speed in-vehicle camera or the like. If information (fourth biological information) related to visual line movement or blinking can be acquired from the image using image processing, the biological electrode or six-axis sensor may not be provided. In this case, the acquiring unit 312 acquires an image of user blinking from the in-vehicle camera. The distribution calculating unit 314 calculates the size of the eye opening (eye-opening level) from the acquired blinking image of the user. For example, the distribution calculating unit 314 executes a binarization process with a skin color of the blinking image of the user as a threshold value, and then calculates a maximum width of upper and lower eyelids or eyeball opened portion area as the size of the eye opening of the user.

FIG. 8 is a graph showing a distribution of eye opening sizes acquired from the target user. The distribution calculating unit 314 calculates a moving average of the eye opening sizes, and detects that the user is beginning to close an eye when the eye opening size at 0.1 seconds is 95% or less than the size immediately prior. Furthermore, the distribution calculating unit 314 acquires an image immediately prior to the user beginning to close an eye and an image when the user closes the eye and opens the eye to a point where the eye opening size is a size immediately prior to beginning to close the eye. The distribution calculating unit 314 detects the size of the size of the eye of the user immediately prior to the user beginning to close the eye. The distribution calculating unit 314 measures an eye-closing time indicating a time from the beginning of closing the eye until the eye opens based on a photographing time of an image immediately prior to the beginning of closing an eye and a photographing time of an image when the eye opens to a size immediately prior to the user beginning to close the eye. The height of the ocular potential peak of the examples corresponds to an "eye-opening level indicating an eye opening size of an image prior to beginning closing of a blinking eye". The width of the ocular potential peak of the examples corresponds to an "eye-closing time indicating a time from the beginning of eye closing until eye opening ends". Furthermore, the distribution calculating unit 314 similarly calculates a histogram having as axes the eye-opening level indicating an eye opening size of an image prior to beginning closing of a blinking eye and eye-closing time indicating a time from the beginning of eye closing until eye opening ends. The processes of the distribution calculating unit 314 and degree of arousal calculating unit 316 are the same for ocular potential distribution.

Note that in the examples, a case was described where a sensor signal from the six-axis sensor 206 mounted on the eyewear 30 was used. However, the application described in the examples can be executed even if a sensor signal from the six-axis sensor 111 mounted to the information processing device 10 is used. In other words, a six-axis sensor may be mounted not only to the head but also at any position on a human body.

Furthermore, in the examples, a case was described where blinking, visual line movement, and body movement were used as biological information. However, biological information such as heart rate, pulse, or the like may also be used in addition thereto. Furthermore, in the examples, a case where a user during operation was used as an example was described. However, the present invention is not limited thereto, and the user may perform daily activities (during holiday, work).

Furthermore, in the examples, a configuration where the information processing device 10 is provided with the distribution calculating unit 314 and degree of arousal calculating unit 316 was described. However, the present invention is not limited thereto, and the configuration may be such that the server 40 is provided therewith.

Furthermore, in the examples, ocular potential distribution was calculated by a histogram of the projection axis and distance L for the measurement points of the ocular potential. However, the present invention is not limited thereto. The measurement points of the ocular potential may be projected on an X axis or Y axis parallel to the projection axis to calculate the ocular potential distance by a histogram of a distance between the projection axis and an intersection between the X axis and Y axis The present invention was described above using examples. However, the technical scope of the present invention is not limited to the scope described in the examples. It is clear to a person with ordinary skill in the art that various modifications and improvements can be added to the aforementioned examples. It is clear from the description of the scope of the patent claims that an embodiment with those modifications and improvements added can be included in the technical scope of the present invention.

DESCRIPTION OF CODES

10 Information processing device
20 Processing device
30 Eyewear
40 Server
302 Storing unit
304 Communicating unit
306 Control unit
312 Acquiring unit
314 Distribution calculating unit
316 Degree of arousal calculating unit

The invention claimed is:

1. An information processing method executed by a computer, comprising the steps of:
    acquiring first biological information related to a height and width of a peak of an ocular potential of a user, the ocular potential being detected by an electrode incorporated into an apparatus attached to a face or a head of the user; and
    calculating a score of a degree of arousal of the user based on a distance between a projection axis and a point in a coordinate space,
    wherein the projection axis is parallel to an equal degree of arousal line in the coordinate space,
    wherein the point indicates a point where a peak of the ocular potential obtained by the first biological information is plotted in the coordinate space, and
    wherein the coordinate space is made by a first axis representing a height of the peak and a second axis representing a width of the peak.

2. The information processing method according to claim 1, wherein the equal degree of arousal line is a straight line determined based on each point where a peak of the ocular potential obtained by second biological information related to a height and width of the peak of the ocular potential acquired from an other user with the same degree of arousal is plotted in the coordinate space.

3. The information processing method according to claim 2, further comprising:
    a step of calculating a histogram related to a distance between the projection axis and a point where a peak of the ocular potential obtained by third biological information is plotted in the coordinate space, the third biological information being related to a height and width of the peak of an ocular potential of the user acquired in a predetermined period before acquiring the first biological information;
    wherein the step of calculating the score of the degree of arousal calculates the score of the degree of arousal based on the histogram and a distance between the projection axis and the point where the peak of the ocular potential obtained by the first biological information is plotted.

4. The information processing method according to claim 1, further comprising:
    a step of calculating a histogram related to a distance between the projection axis and a point where a peak of the ocular potential obtained by third biological information is plotted in the coordinate space, the third biological information being related to a height and width of a peak of an ocular potential of the user acquired in a predetermined period before acquiring the first biological information;
    wherein the step of calculating the score of the degree of arousal calculates the score of the degree of arousal based on the histogram and a distance between the projection axis and the point where the peak of the ocular potential obtained by the first biological information is plotted.

5. An information processing device including a processor, wherein the processor is configured to execute to:
    acquire first biological information related to a height and width of a peak of an ocular potential of a user, the ocular potential being detected by an electrode incorporated into an apparatus attached to a face or a head of the user; and calculate a score of a degree of arousal of the user based on a distance between a projection axis and a point in a coordinate space, wherein the projection axis is parallel to an equal degree of arousal line in the coordinate space, wherein the point indicates a point where a peak of the ocular potential obtained by the first biological information is plotted in the coordinate space, and wherein the coordinate space is made by a first axis representing a height of the peak and a second axis representing a width of the peak.

6. A non-transitory computer readable recording medium storing instructions configured to cause a computer to execute the steps of:

acquiring first biological information related to a height and width of a peak of an ocular potential of a user, the ocular potential being detected by an electrode incorporated into an apparatus attached to a face or a head of the user; and calculating a score of a degree of arousal of the user based on a distance between a projection axis and a point in a coordinate space, wherein the projection axis is parallel to an equal degree of arousal line in the coordinate space, wherein the point indicates a point where a peak of the ocular potential obtained by the first biological information is plotted in the coordinate space, and wherein the coordinate space is made by a first axis representing a height and a second axis representing a width of the peak.

7. An information processing method executed by a computer, comprising the steps of:

sequentially acquiring biological information related to an image of blinking of a user from a camera that photographs the user; and calculating a score of a degree of arousal of the user based on a distance between a projection axis parallel to an equal degree of arousal line in a coordinate space and a point where an eye-opening level and an eye-closing time calculated based on the biological information is plotted in the coordinate space, wherein the coordinate space is made by a first axis representing the eye-opening level indicating the degree that an eye is opened in an image before closing of the blinking of the eye begins and a second axis representing the eye-closing time indicating a time from a first image showing the beginning of closing of the eye to a second image showing the end of opening of the eye.

8. An information processing device including a processor, wherein the processor is configured to execute to:

sequentially acquire biological information related to an image of blinking of a user from a camera that photographs the user; and calculate a score of a degree of arousal of the user based on a distance between a projection axis parallel to an equal degree of arousal line in a coordinate space and a point where an eye-opening level and an eye-closing time calculated based on the biological information is plotted in the coordinate space, wherein the coordinate space is made by a first axis representing the eye-opening level indicating the degree that an eye is opened in an image before closing of the blinking of the eye begins and a second axis representing the eye-closing time indicating a time from a first image showing the beginning of closing of the eye to a second image showing the end of opening of the eye.

9. A non-transitory computer readable recording medium storing instructions configured to cause a computer to execute the steps of:

sequentially acquiring biological information related to an image of blinking of a user from a camera that photographs the user; and calculating a score of a degree of arousal of the user based on a distance between a projection axis parallel to an equal degree of arousal line in a coordinate space and a point where an eye-opening level and an eye-closing time calculated based on the biological information is plotted in the coordinate space, wherein the coordinate space is made by a first axis representing the eye-opening level indicating the degree that an eye is opened in an image before closing of the blinking of the eye begins and a second axis representing the eye-closing time indicating a time from a first image showing the beginning of closing of the eye to a second image showing the end of opening of the eye.

* * * * *